United States Patent [19]

Khoobiar

[11] 4,374,759

[45] Feb. 22, 1983

[54] CATALYSTS AND PROCESS FOR UNSATURATED ALDEHYDES

[75] Inventor: Sargis Khoobiar, Kinnelon, N.J.

[73] Assignee: The Halcon SD Group, Inc., New York, N.Y.

[21] Appl. No.: 327,848

[22] Filed: Dec. 7, 1981

Related U.S. Application Data

[63] Continuation of Ser. No. 939,645, Sep. 5, 1978, abandoned.

[51] Int. Cl.$^3$ .......................... B01J 23/82; B01J 21/00
[52] U.S. Cl. .................................. 252/455 R; 252/456; 252/464
[58] Field of Search ..................... 252/456, 455 R, 464

[56] References Cited

U.S. PATENT DOCUMENTS 4,035,418 7/1977 Okada et al. ..................... 252/456 X
4,087,382 5/1978 Khoobiar ......................... 252/455 R
4,111,984 9/1978 Ishii et al. ........................ 252/456 X

FOREIGN PATENT DOCUMENTS 1456752 11/1976 United Kingdom .

Primary Examiner—Carl F. Dees
Attorney, Agent, or Firm—William C. Long; Riggs T. Stewart; Harold N. Wells

[57] ABSTRACT

A catalyst composition useful for the oxidation of olefins, particularly the vapor phase oxidation of isobutylene and/or tertiary butyl alcohol to produce methacrolein, consists essentially of the combination of oxides of molybdenum, cobalt, iron, bismuth, thallium, antimony, silicon, and nickel, along with one or more members of the groups consisting of the alkali metals, the alkaline earth metals, the rare earth metals including lanthanum, tungsten, and mixtures thereof. The catalyst has a BET surface area within the range of about 0.5–10 m$^2$/gm and preferably within the range of about 2–6 m$^2$/gm. Preferably, the catalyst has no more than about 3% of the surface area associated with pores smaller than about 100 A°. The catalyst is heated during its preparation to a temperature above 525° C., preferably above 550° C., most preferably to about 600° C., for a time sufficient to achieve the desired surface area and pore size distribution and thereby to improve selectivity to methacrolein.

7 Claims, No Drawings

CATALYSTS AND PROCESS FOR UNSATURATED ALDEHYDES

This is a continuation, of application Ser. No. 939,645 filed Sept. 5, 1978, now abandoned.

PRIOR ART

This invention relates to catalysts, and is more particularly concerned with catalysts for the vapor-phase oxidation with molecular oxygen of isobutylene and/or tertiary butyl alcohol to produce methacrolein and to a process for using such catalysts.

It is well known that unsaturated aldehydes, such as acrolein and methacrolein, can be produced by the vapor-phase oxidation of the corresponding olefins by means of molecular oxygen in the presence of a suitable oxidation catalyst. A variety of catalyst compositions have been proposed for this purpose and many such compositions comprise the oxides of molybdenum, iron, and bismuth in particular. As a general rule, however, the selectivity to the desired aldehyde, i.e., the molar quantity of aldehyde obtained per mol of olefin converted, has been relatively low when catalyst compositions of this type have been employed. More recently, attempts have been made to increase the selectivity of the reaction by incorporating oxides of more unusual elements in the catalyst.

In U.S. Pat. No. 4,087,382, an improved catalyst is disclosed which includes the elements molybdenum, bismuth, iron, cobalt, thallium, antimony, and optionally silicon. Such catalysts have been found to have improved performance over catalysts of the prior art. However, further improvements were still sought since, when such catalysts are operated at above-atmosphere pressures, as is typical of commercial practice, inferior results are obtained compared to the performance at atmospheric pressure. Regaining the lost performance at above-atmospheric pressure was desirable for a commercially viable catalyst. In addition, an improvement in the long-term stability of the catalyst was desired.

The present invention comprises an improved catalyst of similar composition to that of the commonly assigned U.S. Pat. No. 4,087,382, but with additional elements which have been found to improve the performance, as will be seen in the discussion hereinafter.

The description of the prior art related to catalysts for use in the oxidation of lower olefins to unsaturated aldehydes is difficult in view of the large number of elements which have been found by various researchers to be useful. With regard to the catalyst composition to be disclosed hereinafter, the following U.S. patents are believed to be particularly material.

U.S. Pat. No. 4,034,008 to Kurtz, et al. discloses a catalyst which is potassium free and which contains molybdenum, bismuth, iron, cobalt and/or nickel, antimony and/or ruthenium, and optionally, a trace of chloride. The patented catalyst does not contain thallium, the rare earth metals, the alkali metals, the alkaline earth metals, or tungsten. Although disclosed broadly for oxidation of alpha, beta-unsaturated monolefins to the corresponding aldehydes or carboxylic acids or for ammoxidation of the same olefins to the corresponding nitriles, the working examples only disclose the oxidation of propylene to acrolein. It should be noted that, although propylene and isobutylene are chemically related, the oxidation of isobutylene (or its equivalent, tertiary butyl alcohol) is considered the more difficult reaction to carry out. Although the catalysts are disclosed to be calcined at 400°-550° C. for 2 to 24 hours, the working examples show the catalysts to be calcined at temperatures in the range of 450°-490° C. Also, the catalysts are disclosed to be preferably disposed on a support such as silica, alumina, silicon carbide, zirconia, and titania.

The significance of the use of thallium is indicated in U.S. Pat. No. 3,951,861, Shiraishi, et al., wherein the criticality of the thallium content is shown with relation to a catalyst composition of molybdenum, bismuth, iron, cobalt and/or magnesium and/or manganese, along with nickel, and optionally, phosphorus and a group of other metals, specifically, copper, calcium, strontium, zinc, cadmium, tin and lead. The patentee's catalyst does not contain antimony, the alkali metals, or the rare earth metals. The patent is directed specifically to the oxidation of propylene to acrolein, although a related patent, U.S. Pat. No. 3,928,462, discloses the benefits of small amounts of thallium in a similar catalyst used for the oxidation of isobutylene to methacrolein. The catalysts are generally calcined at temperatures in the range of 525°-550° C. Preferably, they are disposed on a support such as silica, alumina, silicon, carbide, and titania.

Nickel is used in a number of catalysts, in particular the '861 and '008 patents previously mentioned. In U.S. Pat. No. 3,454,630, Yamaguchi, et al., emphasize the benefits of nickel and/or cobalt oxides. The patentees consider nickel and cobalt as equivalents, and suggest that one or the other may be used. The catalyst of the '630 patent lacks the thallium, antimony, silicon, and alkali metals of the instant catalyst and requires the presence of phosphorus. Example 41 of the '630 patent above shows relatively poor catalytic performance with respect to the selectivity to methacrolein.

Silicon has also been indicated to be a useful component of such catalysts as indicated in the '008 patent previously mentioned, along with U.S. Pat. No. 3,186,955 and U.S. Pat. No. 3,855,308. The catalyst of the '955 patent preferably contains barium and more bismuth than molybdenum and lacks the iron, cobalt, thallium, antimony, nickel, and alkali metals of the instant catalyst. The catalyst is disclosed for multiple purposes, including the oxidation of isobutylene to methacrolein. Calcination above about 565° C. was indicated to be detrimental to the catalyst performance. The catalyst of the '308 patent lacks antimony and nickel, but requires tungsten and is said to be calcined at a temperature between 350°-600° C., although a temperature of 450° C. was used generally in the working examples.

In British Pat. No. 1,456,752 a catalyst basically consisting of molybdenum, bismuth, cobalt, and iron was disclosed to be improved by the addition of antimony. The patent teaches that antimony has the effect of improving the selectivity to methacrolein, but lowers activity of the catalyst when it is calcined at temperatures in the range of 500°-550° C. In such a situation, the patentees would add at least one element from a large group of elements including barium and nickel in order to restore the activity lost by adding antimony. The patentees further disclose that if a catalyst is calcined between a temperature of 600°-700° C., improved activity was obtained. To such catalysts, they would add an alkali metal and/or thallium. In the example, the catalysts were generally mixed with silicon carbide powder as a carrier. The patent states that pressure was not critical in the reaction. The patent contains no information with regard to the surface area or the pore diameter of the catalyst disclosed. Silica is not included as an ingredient of the catalyst.

In general, it is believed that the composition of a catalyst of this type cannot be predicted merely by combining the many elements which have been disclosed in the prior art, but that the catalyst performance must be determined experimentally at the expected operating conditions. Consequently, small changes in composition may be very important in achieving improved catalyst performance and particularly in optimizing the catalyst composition to suit a specific reaction and set of operating conditions.

As will be shown in the description of the invention which follows, changes in operating conditions and in methods of preparation may result in a degradation of catalyst performance and make if necessary to add ingredients to a catalyst in order to recover the loss in performance.

SUMMARY OF THE INVENTION

It has been discovered that the conversion of isobutylene and/or tertiary butyl alcohol with high selectivity to methacrolein can be accomplished by carrying out the vapor-phase molecular oxidation in the presence of a catalyst composition which consists essentially of the oxides of molybdenum, cobalt, iron, bismuth, thallium, antimony, silicon, nickel, and one or more members of the group consisting of the alkali metals, the alkaline earth metals, the rare earth metals including lanthanum, tungsten, and mixtures thereof.

The catalyst composition of the invention may be expressed by the following general formula:

$$Mo_aCo_bFe_cBi_dTl_eSb_fSi_gNi_hX_iO_j$$

wherein X is at least one member of the group consisting of the alkali metals, the alkaline earth metals, the rare earth metals including lanthanum, tungsten, and mixtures thereof and where a to j indicate the atomic ratio of each component so that where a is 12, b is 0.2–8, c is 0.05–5, d is 0.2–4, e is 0.01–5, f is 0.01–5, g is 1–20, h is 0.05–5, i is a positive value up to 4, and j has a value which is determined by the valence and proportions of the other elements in the catalyst.

More specifically, a preferred catalyst composition according to the invention comprises the oxides of the specified elements in the following atomic ratios: Mo=12, Co=4, Fe=3, Bi=1, Tl=0.5, Sb=0.3, Si=6.6, Ni=2, Cs=0.3, and K=0.3, based on the composition of the original solutions. The catalyst composition may be regarded either as a mixture of oxides of the named elements or as oxygen-containing compounds of the elements and the use of the phrase "mixture of oxides" shall be understood to include either or both forms. As prepared and/or under the reaction conditions, the catalyst may contain either or both forms.

The catalyst is prepared by methods generally known in the art, but is calcined at higher temperatures than those generally employed heretofore, namely, at least above 525° C. and preferably above 550° C. After calcination for a sufficient period of time, the catalyst of the invention will have a BET surface area within the range of about 0.5–10 m²/gm, preferably within the range of about 2–6 m²/gm and will have no more than about 10% of the pore volume, preferably about 3%, associated with pores smaller than about 100 A°.

In another aspect, the invention includes a process for the vapor-phase oxidation of isobutylene and/or tertiary butyl alcohol to produce methacrolein in the presence of the catalyst described above.

DESCRIPTION OF THE PREFERRED EMBODIMENTS

Catalyst Composition and Preparation

The catalyst of the invention consists essentially of the oxides of molybdenum, cobalt, iron, bismuth, thallium, antimony, silicon, nickel and one or more members of the groups consisting of the alkali metals, the alkaline earth metals, the rare earth metals including lanthanum, tungsten, and mixtures thereof and having the following general formula:

$$Mo_aCo_bFe_cBi_dTl_eSb_fSi_gNi_hX_iO_j$$

wherein X is at least one member of the group consisting of the alkali metals, the alkaline earth metals, the rare earth metals, lanthanum, tungsten, and mixtures thereof and where a to j indicate the atomic ratio of each component so that where a is 12, b is 0.2–8, c is 0.05–5, d is 0.2–4, e is 0.01–5, f is 0.01–5, g is 1–20, h is 0.05–5, i is a positive value up to 4, and j has a value which is determined by the valence and proportions of the other elements in the catalyst.

The catalyst composition is calcined at a temperature of at least 525° C. for a period of time sufficient to reduce the BET surface area to between about 0.5 to about 10 m²/gm of catalyst. Preferably the BET surface area will be between about 2 and about 6 m²/gm of catalyst and no more than about 3% of the surface will be associated with pores having a diameter smaller than 100 A°. The BET surface area is measured by the nitrogen adsorption method described by Brunauer, Emmett, and Teller in the "Journal of the American Chemical Society", Vol 60, page 309 (1938). The pore diameter and volume are determined by the mercury porosimeter method described by Drake and Ritter in "The Analytical Edition of Industrial Engineering Chemistry", Vol 17, page 787 (1945). The surface area, pore size, and pore volume are frequently interrelated by the equation given by Emmett and DeWitt in "The Analytical Edition of Industrial Engineering Chemistry", Vol 13, page 28 (1941).

The catalyst composition is preferably used in the form of pellets or other like compressed shapes of various sizes. The composition may be formed in conventional manner using techniques well known to persons skilled in the art. For example, compounds of molybdenum, cobalt, iron, thallium, antimony, bismuth, cesium, potassium and nickel are each dissolved in a small amount of water or other solvent, and the solutions are then combined with colloidal silica and the mixture evaporated to dryness. To prepare the catalyst, the several components can be introduced into the solution in the form of various salts or other compounds of convenient types and no specific form for the catalyst precursors is necessary. The use of ammonium salts, halides, e.g. chlorides, nitrates, or acid forms of the elements to be supplied are, however, particularly suitable. Preferably, however, aqueous solutions are employed and water-soluble forms of the elements are used, except that the silica portion of the catalyst is normally insoluble. In some cases, the solutions may have acids and/or bases added to them to facilitate dissolution of the catalyst precursors. For example, acids such as hydrochloric or nitric or bases such as ammonium hydroxide can be used if desired. Silicon may be added in the form of an aqueous colloidal solution of $SiO_2$. Typical suspensions of colloidal silica particles in water or alcohol are available from Nalco Chemical Company (Nalcoag®), and E. I. DuPont de Nemours (Ludox®). Colloidal silica is also available in powder form from Degussa (Aerosil®). The particles may range from about 600 A° size which have a BET surface area of $50^2$m/gm, to particles of 40 A° size, which have a BET surface area of 750 $m^2$/gm.

The powder resulting after evaporation is thoroughly dried and preferably screened to eliminate large particles which would hinder formation of uniform compressed shapes, such as pellets. Typically, the powder is passed through a 20-mesh (Tyler) screen. The powder is then mixed with an organic binder of any conventional type, such as polyvinyl alcohol, and the mixture is thoroughly dried and again screened, typically to provide 20-80 mesh (Tyler) size particles. The dried particles are then preferably combined with a lubricant, again of any conventional type, such as stearic acid or graphite, and compressed into the desired shape, e.g. pelletized, or extruded or otherwise shaped, the compressed shapes typically having heights and diameters of 1/16 inch to ⅜ inch. Finally, the thus-produced catalyst composition is activated at a higher temperature than has generally been used for prior art catalysts and for a prolonged period as required to obtain the desired BET surface area. For example and typically, the pellets are placed in an oven or kiln, or in a tube through which air is passed, at an elevated temperature (e.g. at least 525° C., preferably above 550° C.) for two to ten hours. In a particularly preferred activation step, the temperature is raised at the rate of 20° C. per hour to 600° C. and this temperature is maintained for 3 hours.

It will be understood that the foregoing description regarding preparation of the catalyst in a form suitable for use in a vapor-phase oxidation reaction is merely illustrative of many possible preparative methods and is given solely by way of exemplification, except that the calcination portion of the preparation procedure is an important aspect of the present invention. This method is, however, particularly suitable and is preferred.

USE OF THE CATALYST

The catalyst and the processes of the present invention are useful generally for the production of unsaturated aldehydes by oxidation with molecular oxygen of lower olefins and the ammoxidation of olefins. The preferred starting materials are the monoethylenically unsaturated olefins having 3 or 4 carbon atoms, or mixtures of olefins. As previously noted, catalysts are specifically developed for optimum performance with particular feed stock and operating conditions. Thus, the catalyst disclosed and claimed herein is especially suited to the oxidation of isobutylene and/or tertiary butyl alcohol to methacrolein.

When the catalyst of this invention is used in the vapor-phase oxidation of isobutylene and/or tertiary butyl alcohol to form methacrolein, the operating conditions employed are those generally associated with this reaction. Thus, the reaction in which the catalyst compositions of this invention are of particular utility and in which they provide high selectivity involves contacting isobutylene and/or tertiary butyl alcohol in the vapor phase with the catalyst and molecular oxygen, preferably also in the presence of steam. Once reaction is begun, it is self-sustaining because of its exothermic nature. A variety of reactors will be found to be useful and the common multiple tube heat exchanger type in which the catalyst pellets are disposed inside the tubes is satisfactory. The process can be carried out in conventional equipment commonly employed for reactions of this type.

The gaseous feed to the reactor contains relatively low concentrations of olefin, oxygen and steam. Typically, an inert gas, such as nitrogen, is also present. The oxygen is usually added as such, or as air, or as air enriched with oxygen. As mentioned, conventional oxidation conditions can be employed but, for best results, the olefin is generally present in concentrations of about 2 to 20 volume percent of the total feed with a preferred range of about 5 to 15 volume percent, and the corresponding ranges for oxygen are 4 to 30 volume percent (as limited by the flammable range of mixtures) and preferably 10-20 volume percent and for steam up to 30 volume percent, and preferably 5 to 25 volume percent, the balance being the inert gas or gases.

The temperature of the reaction should, for best results, be within the range of from about 250° to 500° C., preferably 300° to 400° C., and the optimum temperature range is 310° to 370° C. Because the reaction is exothermic, means for conducting the heat away are normally employed, such as by surrounding tubes containing catalyst pellets with a salt bath or with boiling water.

The pressure in the reactor has an effect on the catalyst performance as will be seen later. While the reaction may be conducted at atmospheric, superatmospheric, or subatmospheric pressure, preferably pressures ranging from atmospheric up to 15.1 kg/cm² absolute, preferably up to 8 kg/cm² absolute, and most preferably up to 6.3 kg/cm² absolute are employed. Typically, a pressure of about 3.4 kg/cm² absolute is used.

The methacrolein product may be recovered by various methods known to those skilled in the art. For example, the methacrolein may be condensed, or scrubbed with water or other suitable solvents, followed by separation of the unsaturated aldehyde product from the scrubbing liquid. The gases remaining after the methacrolein-removal step may be recycled to the reaction, if desired, and in such case the net $CO_2$ produced by the reaction may be removed by conventional means, such as absorption in an aqueous carbonate solution, or purged from the system.

The features of the invention will be more readily apparent from the following specific examples. It will be understood, however, that these examples are for the purpose of illustration only and are not to be interpreted as limiting the invention.

EXAMPLE 1

Prior Art

In 750 cc of water are dissolved 636 grams of the molybdenum salt $(NH_4)_6Mo_7O_{24}.4H_2O$. Then 262 grams of $Co(NO_3)_2.6H_2O$ are dissolved in 300 cc of water, 60.6 grams of $Fe(NO_3)_3.9H_2O$ are dissolved in 200 cc of water, 79.8 grams $Tl NO_3$ are dissolved in 400 cc of water, 68.4 grams of $Sb Cl_3$ are dissolved in a mixture of 100 cc of water, and 30 cc of concentrated HCl, and 275 grams of $Bi(NO_3)_3.5H_2O$ are dissolved in a mixture of 200 cc of water and 50 cc of concentrated nitric acid. Sufficient ammonium hydroxide is added to bring the pH of the solution to a value of 7. These solutions are fed to a rotary dryer of 4000 cc capacity and the mixture in the dryer is evaporated to dryness and the temperature raised to 300° C. The resulting powder is removed from the dryer and dried in an oven at 400° C. for 12 hours. The dried powder is screened through a 20-mesh screen, a 4% aqueous solution of polyvinyl alcohol is added in sufficient quantity to make a damp mixture and this mixture is dried at 75°-80° C. until the moisture content reaches 2-4%. The dried mixture is then screened to 20-60 mesh, and about 2% of stearic acid powder is thoroughly mixed with it. The resulting mixture is then pelletized to form pellets of 3/16 inch height and diameter. The pellets are then activated in an oven by heating them gradually at a rate of 20° C. per hour to about 380° C. and maintaining them at this temperature for 16 hours. The activated pellets have a density of 0.95 gm/cc, a surface area of 6.5 m$^2$/cm. The catalyst components molybdenum, cobalt, iron, thallium, antimony, and bismuth, based on the amounts in the original solutions, are in the atomic ratios of 12, 3, 0.5, 1, 1, and 1.5, respectively.

A 50 cc quantity of this catalyst composition is placed in a reactor defined by a ½"×108" stainless steel pipe, the reactor pipe being filled with 300 cc of inert filler (silicon carbide) below the catalyst bed and sufficient inert filler above the catalyst bed to fill the reactor. Nitrogen-diluted mixtures containing 9 vol % isobutylene, 10 vol % oxygen, and 20 vol % steam are fed to the reactor at a pressure about one atmosphere, at temperatures ranging from 360°-370° C. and at a space velocity of about 3000 hr$^{-1}$. The term "space velocity" is used in its conventional sense to mean liters of gas (Standard Temperature and pressure) per liter of catalyst per hour. The reaction is run with continuous introduction of feed and continuous withdrawal of exit gas. The exit gas is analyzed at intervals of several hours by means of gas chromatography except for measurement of CO/CO$_2$ by infra-red absorption, using conventional techniques. The combined production of methacrolein and methacrylic acid is reported since both products are useful and, in general, the methacrolein will be separated and oxidized in a separate reactor to form additional methacrylic acid, typically for conversion to methyl methacrylate. The predominant product is methacrolein and the amount of methacrylic acid present is only about 2-3% of the total shown below. The experimental results are reported in Table I.

TABLE I

| Test No. | Time, hr. | Isobutylene Conversion, % | Selectivity, % | | |
|---|---|---|---|---|---|
| | | | Methacrolein + Methacrylic Acid | Acetic Acid | CO + CO$_2$ |
| 1 | 12 | 55.0 | 86.9 | 2.4 | 4.7 |
| 2 | 62 | 54.0 | 88.5 | 1.7 | 4.8 |
| 3 | 172 | 61.8 | 86.8 | 1.54 | 4.34 |
| 4 | 177 | 60.0 | 87.8 | 1.76 | 3.70 |
| 5 | 180 | 59.2 | 87.4 | 1.9 | 3.80 |
| 6 | 210 | 61.6 | 86.0 | 1.51 | 4.80 |
| 7 | 214 | 65.3 | 87.4 | 1.35 | 3.91 |
| 8 | 231 | 67.3 | 88.8 | 1.85 | 2.47 |
| 9 | 235 | 59.1 | 87.5 | 1.65 | 3.32 |
| 10 | 238 | 58.6 | 87.4 | 1.42 | 3.65 |
| 11 | 255 | 60.7 | 87.6 | 1.48 | 3.71 |
| 12 | 261 | 57.6 | 87.2 | 1.60 | 3.63 |
| 13 | 279 | 63.4 | 86.5 | 1.89 | 3.78 |
| 14 | 285 | 57.1 | 85.0 | 2.05 | 4.11 |
| 15 | 306 | 57.2 | 86.9 | 1.80 | 3.59 |
| 16 | 308 | 63.2 | 85.1 | 1.86 | 4.08 |

EXAMPLE 2

A catalyst having the same composition as that of Example 1 and a surface area of 5.6 m$^2$/gm is tested. The pressure of the reaction is increased to 3.46 kg/cm$^2$ absolute, which results in a reduction in conversion and selectivity to methacrolein as will be seen in Table II. The space velocity of the feed gas was 3000 hr$^{-1}$ and the composition of the gas was essentially the same as in Example 1, except that 8.5 vol % tertiary butyl alcohol (TBA) was submitted for the isobutylene feed used in Example 1, with the result that after dehydration the composition of the gas was 7 vol % isobutylene, 9.8 vol % oxygen, and 20 vol % steam, with the remainder being nitrogen. The temperature ranged between 335°-340° C.

It will be observed from a comparison of Tables I and II that increasing the pressure of the reaction resulted in an inferior performance, as indicated by the poorer selectivity to the desired product, methacrolein and the increase of by-product, acetic acid and CO/CO$_2$. Since conversion was lower in this example, selectivity would be expected to be higher than that of Table I, if the increased pressure had not had an effect. This inferior performance at higher pressure was found even though the catalyst of Table II had not been used as long as the catalyst of Table I, which might have suffered some loss in performance with time. It may be concluded that the oxidation of isobutylene and/or tertiary butyl alcohol (they are considered to be equivalent feed stocks) to methacrolein is sensitive to increases in pressure in this relatively low range. It will be appreciated that a pressure above atmospheric would normally be used and that the pressure of 3.46 kg/cm$^2$ absolute used in Example 2 is a more realistic value for industrial applications.

TABLE II

| Test No. | Time, hr. | TBA Conversion, % | Selectivity, % | | |
|---|---|---|---|---|---|
| | | | Methacrolein + Methacrylic Acid | Acetic Acid | CO + CO$_2$ |
| 17 | 38 | 46 | 76.5 | 6.1 | 13.2 |
| 18 | 54 | 51 | 75.8 | 5.2 | 13.3 |
| 19 | 56 | 50 | 76.5 | 5.4 | 12.3 |
| 20 | 58 | 46 | 77.4 | 5.0 | 11.4 |
| 21 | 60 | 47 | 78.3 | 4.7 | 10.8 |
| 22 | 66 | 43 | 77.5 | 4.4 | 12.3 |
| 23 | 68 | 46 | 78.3 | 4.7 | 11.1 |
| 24 | 80 | 60 | 79.3 | 5.0 | 9.8 |
| 25 | 82 | 60 | 77.3 | 5.5 | 10.9 |
| 26 | 86 | 50 | 78.9 | 4.4 | 11.0 |
| 27 | 92 | 45 | 79.7 | 4.4 | 10.6 |
| 28 | 96 | 60 | 76.3 | 5.2 | 13.1 |
| 29 | 100 | 61 | 76.9 | 6.1 | 12.1 |
| 30 | 104 | 61 | 77.7 | 5.6 | 11.7 |
| 31 | 108 | 57 | 79.1 | 5.5 | 10.5 |
| 32 | 118 | 51 | 79.4 | 5.0 | 10.4 |
| 33 | 122 | 52 | 80.5 | 4.4 | 10.0 |
| 34 | 126 | 51 | 79.2 | 4.9 | 10.6 |
| 35 | 130 | 50 | 78.8 | 4.8 | 11.1 |

EXAMPLE 3

Example 2 is repeated except that in making the catalyst, it is heated to about 600° C. rather than the 380° C. used in Example 2. The surface area of the catalyst is found to be 2.4 m$^2$/gm. The feed gas composition was 5.7 vol. % TBA, 9.8 vol % oxygen, 20% steam, and the remainder nitrogen. It is found that a temperature of 435°-445° C. is required to obtain a conversion of 33-36% and a selectivity to methacrolein plus methacrylic acid of about 75.5%. The CO+CO₂ selectivity is found to be about 20%. Thus, heating the catalyst to a temperature of 600° C., instead of the 380° C. of Example 2, results in a significant deterioration of catalyst performance.

EXAMPLE 4

In 750 cc of water are dissolved 636 grams of the molybdenum salt $(NH_4)_6Mo_7O_{24}\cdot 4H_2O$. Then 349 grams of $Co(NO_3)_2\cdot 6H_2O$ are dissolved in 400 cc of water, 363 grams of $Fe(NO_3)_3\cdot 9H_2O$ are dissolved in 400 cc of water, 175 grams of $Ni(NO_3)_2\cdot 6H_2O$ are dissolved in 300 cc of water, 40 grams of Tl NO₃ are dissolved in 400 cc of water, 17.4 grams of $CsNo_3$ are dissolved in 100 cc of water, 6 grams of KOH are dissolved in 50 cc of water, 20.4 grams of $SbCl_3$ are dissolved in 30 cc of water and 10 cc of concentrated HCl, and 145 grams of $Bi(NO_3)_2\cdot 5H_2O$ are dissolved in 100 cc H₂O and 25 cc of concentrated nitric acid. To all the above solutions in admixture, 300 grams of 40% colloidal silicon dioxide (Ludox HS 40%, obtained from E. I. DuPont de Nemours and having an average particle size of 120 A° and a BET surface area of 232 m²/gm) are added. Sufficient ammonium hydroxide is added to bring the pH of the solution to a value of 7. Then the solution is evaporated to dryness and prepared as pellets in the manner described in Example 1, except that the pellets are activated by heating in air at a rate of 20° C. per hour to about 340° C. and then heated rapidly to 600° C. and held at that temperature for 2.5 hours. The finished catalyst has atomic ratios of molybdenum, cobalt, iron, bismuth, thallium, antimony, silicon, nickel, cesium, and potassium of 12, 4, 3, 1, 0.5, 0.3, 6.6, 2, 0.3 and 0.3, respectively, based on the composition of the original solutions. During activation, the surface area is reduced from about 23 m²/gm to 5.1 m²/gm.

The catalyst was tested under the conditions of Example 3, except that a temperature of only about 335° C. was needed to obtain the superior results shown in Table III. The catalyst is superior to the results of Example 2 and also of Example 1, which was carried out at the more favorable pressure of one atmosphere.

TABLE III

| Test No. | Time, hr. | TBA Conversion, % | Selectivity, % Methacrolein + Methacrylic Acid | Acetic Acid | CO + CO₂ |
|---|---|---|---|---|---|
| 36 | 12 | 67 | 84.7 | 2.4 | 6.3 |
| 37 | 18 | 70 | 83.9 | 2.3 | 7.5 |
| 38 | 22 | 70 | 84.2 | 2.2 | 7.1 |
| 39 | 26 | 72 | 84.2 | 3.3 | 5.0 |
| 40 | 34 | 70 | 84.9 | 2.2 | 6.6 |
| 41 | 38 | 70 | 85.2 | 2.4 | 6.4 |
| 42 | 60 | 71 | 83.8 | 2.7 | 6.2 |
| 43 | 100 | 68 | 84.2 | 2.1 | 7.6 |
| 44 | 2000 | 68 | 84.4 | 2.4 | 6.5 |

It can be seen that the catalyst of Example 1 with added nickel, silica, cesium, and potassium has superior performance compared to the prior art catalyst of Example 1, but under the more severe conditions of Example 3.

EXAMPLE 5

Similar results are shown in the following Table IV in which a catalyst having the same composition as Example 4 is prepared, except that the silicon content is raised from an atomic content of 6.6 to 12. The surface area of the catalyst was reduced from about 23 m²/gm to 7.8 m²/gm by heating to 600° C. during preparation of the catalyst. In contrast to the previous examples, the feed composition, pressure, and space velocity were varied during the test run.

EXAMPLE 6

The effect of nickel on the catalyst of the invention is shown in the following Table V in which the catalyst composition of Example 4, but excluding the nickel content, is tested under the same conditions as in Example 4.

TABLE V

| Test No. | Time, hr. | Temp. °C. | TBA Conv. % | Selectivity, % Methacrolein + Methacrylic Acid | Acetic Acid | CO + CO₂ |
|---|---|---|---|---|---|---|
| 60 | 9 | 368 | 65 | 82.5 | 3.1 | 9 |
| 61 | 11 | 368 | 66 | 83.3 | 3.3 | 8 |
| 62 | 13 | 366 | 64 | 83.6 | 2.9 | 8.9 |
| 63 | 19 | 372 | 68 | 80.9 | 3.2 | 11 |

TABLE IV

| Test No. | Time, hr. | Feed Gas Composition Vol. % iC₄ | O₂ | H₂O | Pressure Atm. | Temp. °C. | Space Velocity hr⁻¹ | iC₄ Conv. % | Selectivity, % Methacrolein + Methacrylic Acid |
|---|---|---|---|---|---|---|---|---|---|
| 45 | 6 | 5.7 | 16 | 20 | 2.36 | 364 | 1000 | 72.6 | 81.3 |
| 46 | 9 | 5.7 | 16 | 20 | 2.36 | 379 | 1000 | 74.5 | 79.4 |
| 47 | 24 | 5.7 | 9 | 16 | 3.38 | 362 | 3000 | 46.7 | 85.6 |
| 48 | 26 | 5.7 | 9 | 16 | 3.38 | 362 | 3000 | 50.8 | 83.4 |
| 49 | 35 | 5.7 | 9 | 16 | 3.38 | 341 | 3000 | 39.4 | 85.1 |
| 50 | 48 | 5.7 | 9 | 16 | 3.38 | 355 | 3000 | 45.5 | 84.9 |
| 51 | 51 | 5.7 | 9 | 16 | 3.38 | 356 | 3000 | 46.1 | 84.1 |
| 52 | 60 | 5.7 | 9 | 16 | 3.38 | 365 | 3000 | 49.9 | 84.1 |
| 53 | 79 | 5.7 | 9 | 16 | 3.38 | 360 | 3000 | 50.3 | 86.0 |
| 54 | 81 | 5.7 | 9 | 16 | 3.38 | 365 | 3000 | 50.4 | 84.4 |
| 55 | 96 | 5.7 | 9 | 16 | 3.38 | 379 | 3000 | 53.9 | 85.1 |
| 56 | 116 | 7 | 16 | 15 | 2.36 | 380 | 2250 | 49.3 | 83.4 |
| 57 | 119 | 7 | 16 | 15 | 2.36 | 380 | 2250 | 51.7 | 83.4 |
| 58 | 122 | 7 | 16 | 15 | 2.36 | 388 | 2250 | 54.9 | 82.4 |
| 59 | 128 | 7 | 16 | 15 | 2.36 | 388 | 2250 | 57.1 | 81.6 |

Comparing Tables III and V, it can be seen that the conversion of tertiary butyl alcohol is lower when the catalyst lacks nickel, as indicated both directly by measurement and indirectly by the temperature required for the reaction. The surface area of the catalyst is 4.8 m²/gm.

EXAMPLE 7

A catalyst is prepared according to Example 4 except that potassium and cesium were replaced by calcium and 52.8 grams of Ca(C₂H₃O₂).H₂O is dissolved in 200 cc of water and added to the solution to provide calcium in a catalyst having the following composition (based on the original solutions):

$$Mo_{12}Co_4Fe_3Bi_1Tl_{0.5}Sb_{0.3}Si_{6.6}Ni_2Ca_1O_j$$

The catalyst is heated to about 600° C. for 3 hours during the calcination which caused the surface area to be reduced from about 20 m²/gm to 5 m²/gm. The catalyst was tested with a feed composition of 7 vol % isobutylene, 15 vol % steam, 16 vol % oxygen, and the remainder nitrogen and a pressure of 2.44 kg/cm² absolute and a space velocity of about 2250 hr⁻¹ with the following results.

TABLE VI

| Test No. | Time, hr. | Temp, °C. | iC₄ Conv. % | Selectivity, % Methacrolein + Methacrylic Acid | Acetic Acid | CO + CO₂ |
|---|---|---|---|---|---|---|
| 64 | 9 | 345 | 66 | 78.2 | 3.7 | 10.7 |
| 65 | 33 | 371 | 75 | 80.8 | 3.7 | 10.6 |
| 66 | 42 | 379 | 84 | 79.7 | 5.2 | 11.2 |
| 67 | 63 | 379 | 87 | 80.7 | 3 | 12.6 |
| 68 | 91 | 351 | 83 | 79.6 | 4 | 11.8 |

EXAMPLE 8

A catalyst is prepared according to Example 4 except that 124 grams of La(NO₃)₃.5H₂O is dissolved in 300 cc of water and added to the solution to provide lanthanum in a catalyst having the following composition (based on the original solutions):

$$Mo_{12}Co_4Fe_3Bi_1Tl_{0.5}Sb_{0.3}Si_{6.6}Ni_2La_1Cs_{0.3}K_{0.3}O_j.$$

EXAMPLE 9

A catalyst prepared according to Example 4 except that 76.2 grams of (NH₄)₆W₇O₂₄.H₂O is dissolved in 300 cc of water and added to the solution to provide tungsten in a catalyst having the following composition (based on the original solutions):

$$Mo_{12}Co_4Fe_3Bi_1Tl_{0.5}Sb_{0.3}Si_{6.6}Ni_2W_1Cs_{0.3}K_{0.3}O_j.$$

In addition to the effect of the revised catalyst composition, it is believed to be important to maintain the catalyst surface area within a relatively narrow range, broadly 0.5–10 m²/gm and preferably 2–6 m²/gm as measured by the BET method. The surface area is related to the pore size since a particle containing many small pores will have a large surface area, and a particle containing only large pores will have a relatively small surface area. Heating the catalyst for a sufficient period of time to a temperature of at least 525° C. and preferably above 550° C. appears to have the effect of eliminating the smaller pores and thus reducing the surface area. Although calcination of the catalyst before use at about 600° C. is preferred, calcination at somewhat lower temperatures, at least about 525° C., can be carried out if the surface area of the finished catalyst is below about 10 m²/gm and preferably below about 6 m²/gm, as will be seen from the following Example 10.

EXAMPLE 10

A catalyst is prepared according to Example 4 to produce a catalyst having the following composition (based on the original solutions):

$$Mo_{12}Co_4Fe_3Bi_1Tl_{0.5}Sb_{0.3}Si_{6.6}Ni_2Cs_{0.3}K_{0.3}O_j.$$

The catalyst is heated to about 550° C. for three hours during calcination which produced a surface area of 9.6 m²/gm the catalyst is tested with a feed composition of 5.4 vol % isobutylene, 9.8 vol % oxygen, 16 vol % steam, and the remainder nitrogen and a pressure of 3.4 kg/cm² absolute, a temperature about 335° C., and a space velocity of about 3000 hr⁻¹ with the following results.

TABLE VII

| Test No. | Time, hr. | iC₄= Conversion, % | Methacrolein + Methacrylic Acid | Acetic Acid | CO + CO₂ |
|---|---|---|---|---|---|
| 69 | 8 | 74.6 | 82.15 | 2.58 | 8.01 |
| 70 | 10 | 73.5 | 82.25 | 2.50 | 8.07 |
| 71 | 12 | 74.2 | 82.73 | 2.54 | 7.83 |
| 72 | 14 | 74.5 | 82.64 | 2.30 | 8.24 |
| 73 | 26 | 68.5 | 82.5 | 2.51 | 8.2 |

EXAMPLE 11

A catalyst having the composition Mo₁₂Co₄Fe₃Bi₁Tl₀.₅ Sb₀.₃Si₆.₆Ni₂Cs₀.₃K₀.₃O_j, is measured to have a total surface area of 23 m²/gm after calcination at temperatures up to 380° C. The pore volume is measured by the mercury porisimeter method to be 0.3 cc/gm and the pore distribution is measured by the same method to be such that 70% of the catalyst internal area belongs to pores 100 A° diameter and larger and 30% of the internal area belongs to pores smaller than 100 A°. The median pore diameter is 1600 A°.

A catalyst was prepared identically to that described above except that it was calcined at 600° C. for three hours in air. The pore volume remains 0.3 cc/gm, but the total surface area is found to be 6.24 m²/gm and 97% of the internal area belongs to pores 100 A° diameter and larger and only 3% of the internal area belongs to pores smaller than 100 A° diameter. The median diameter is 3,660 A°.

As indicated by Example 11, one effect of heating the catalyst to higher than normal temperatures is to reduce the surface area by eliminating the pores having a diameter smaller than about 100 A°, which has the effect of increasing the average pore diameter. Other effects may also be important.

What is claimed is:

1. A catalyst composition suitable for the vapor-phase oxidation of isobutylene and/or tertiary butyl alcohol to produce methacrolein consisting essentially of the oxides of molybdenum, cobalt, iron, bismuth, thallium, antimony, silicon, nickel, and a member of the group consisting of the alkali metals, the alkaline earth metals, the rare earth metals including lanthanum, tungsten, and mixtures thereof and having a BET surface area between about 0.5 and about 10 square meters per gram of catalyst.

2. A catalyst composition as defined in claim 1 which has been calcined in air at a temperature of at least about 525° C. for a period of time sufficient to reduce the BET surface area to the defined values.

3. A catalyst composition as defined in claim 1, having the formula $Mo_aCo_bFe_eBi_dTl_eSb_fSi_gNi_hX_iO_j$, wherein X is one or more members of said group of alkali metals, alkaline earth metals, rare earth metals including lanthanum, tungsten, and mixtures thereof, and where: a=12; b=0.2-8; c=0.05-5; d=0.2-4; e=0.01-5; f=0.01-5; g=1-20; h=0.05-5; i=a positive value up to 4; j is dependent upon the valence and proportions of the other elements.

4. A catalyst composition as defined in claim 3 wherein the BET surface area is between about 2 and about 6 square meters per gram of catalyst and no more than about 3% of the surface of said catalyst is associated with pores having a diameter smaller than 100 Angstroms.

5. A catalyst composition suitable for the vapor-phase oxidation of isobutylene and/or tertiary butyl alcohol to produce methacrolein containing molybdenum, cobalt, iron, bismuth, thallium, antimony, and silicon wherein the improvement comprises adding catalytically effective amounts of nickel and, a member of the group consisting of alkali metals, the alkaline earth metals, the rare earth metals including lanthanum, tungsten, and mixtures thereof, and calcining said catalyst before use in said oxidation at a temperature of at least 525° C. in air for a sufficient period of time to reduce the BET surface area to the range of about 0.5-10 m²/gm.

6. A catalyst composition as defined in claim 5 wherein the BET surface area is between about 2 and 6 square meters per gram of catalyst and no more than about 3% of the surface area of said catalyst is associated with pores having a diameter smaller than 100 Angstroms.

7. A catalyst composition as defined in claim 5 having the formula $Mo_aCo_bFe_cBi_dTl_eSb_fSi_gNi_hX_iO_j$, where X is one or more members of said group of alkali metals, alkaline earth metals, rare earth metals including lanthanum, and tungsten and where: a=12; b=0.2-8; c=0.05-5; d=0.2-4; e=0.01-5; f=0.01-5; g=1-20; h=0.05-5; i=a positive value up to 4; and j is dependent upon the valence and proportions of the other elements.

\* \* \* \* \*

UNITED STATES PATENT AND TRADEMARK OFFICE
CERTIFICATE OF CORRECTION

PATENT NO. : 4,374,759
DATED : February 22, 1983
INVENTOR(S) : Sargis Khoobiar

It is certified that error appears in the above-identified patent and that said Letters Patent are hereby corrected as shown below:

```
Column  2, line 66  -  change "example" to -- examples --;
        3, line 18  -  change "if" to -- it --;
        5, line 11  -  change "50²m/gm" to -- 50 m²/gm --;
        9, line  3  -  change "THus" to -- Thus --;
       13, line  2
          claim 3   -  change "Fe_e" to -- Fe_c --.
```

Signed and Sealed this

Twentieth Day of September 1983

[SEAL]

Attest:

GERALD J. MOSSINGHOFF

Attesting Officer

Commissioner of Patents and Trademarks